United States Patent [19]
Weinhold

[11] 3,994,158
[45] Nov. 30, 1976

[54] HYDRAULICALLY OPERATED WORKPIECE TESTING MACHINE

[75] Inventor: Helmut Weinhold, Ketsch, Rhine, Germany

[73] Assignee: MFL Pruf-und Messsysteme GmbH, Mannheim, Germany

[22] Filed: Feb. 10, 1976

[21] Appl. No.: 656,947

[30] Foreign Application Priority Data
Feb. 14, 1975 Germany............................ 2506237

[52] U.S. Cl. ................................. 73/97; 100/269 R
[51] Int. Cl.² ............................................ G01N 3/10
[58] Field of Search ................ 73/97, 93; 100/269 R

[56] References Cited
UNITED STATES PATENTS
2,080,165  5/1937  Cox..................................... 73/97 X
3,575,045  4/1971  Knights................................ 73/97 X Primary Examiner—Jerry W. Myracle
Attorney, Agent, or Firm—Michael J. Striker

[57] ABSTRACT

Two stationary uprights are mounted on a support and each of them carries a piston. Each upright is surrounded by a vertically movable cylinder whose interior is subdivided by the respective piston with an upper and a lower chamber. Fluid passages are formed in the uprights and each of the latter has two fluid ports which respectively communicate with the upper and the lower chamber of the associated cylinder. A cross-head rigidly connects the cylinders for joint movement.

6 Claims, 1 Drawing Figure

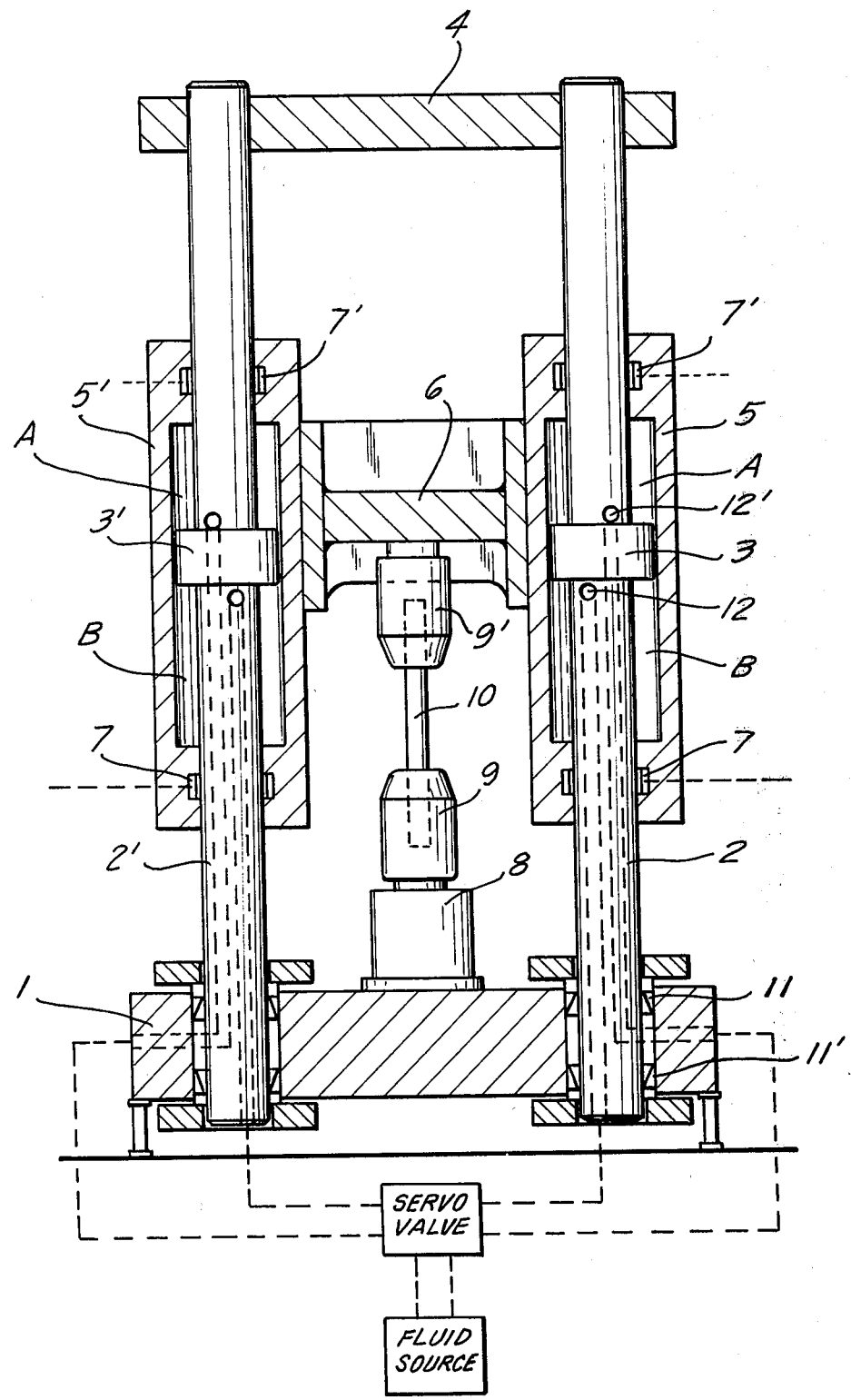

HYDRAULICALLY OPERATED WORKPIECE TESTING MACHINE

BACKGROUND OF THE INVENTION

The present invention relates to a machine for testing workpieces for tensile strength and related factors. In particular, the invention relates to a hydraulically operated machine of this type.

Testing machines of this basic type are known in the art. In these, opposite end portions of a workpiece are connected to two components of the machine, usually a base and a cross-head. The cross-head is adjustable by means of a spindle drive so that it can move towards and away from the base in dependence upon the length of the workpiece. The drive may, for instance, utilize a Leonhard Control with a mechanical drive and a screw spindle. Once the cross-head has reached a desired distance from the base it can be arrested by means of manually operated counter nuts and/or hydraulic clamping devices. This type of machine is generally satisfactory for the intended purpose, but it is relatively complicated and therefore expensive to manufacture and maintain.

SUMMARY OF THE INVENTION

It is therefore an object of the present invention to overcome this problem.

In particular, it is an object of the invention to provide a hydraulically operated workpiece testing machine which is simple in its construction and inexpensive to manufacture and maintain.

A further object of the invention is to provide a machine which is highly reliable and capable of performing at least the same functions as the prior art machines of this general type.

In keeping with these objects, and with others which will become apparent hereafter, one feature of the invention resides in a hydraulically operated workpiece testing machine which, briefly stated, comprises a support element; at least two stationary uprights mounted on the support element and each provided with a piston; at least two floating cylinders, each shiftably surrounding one of the uprights so that the piston thereof is located in the interior of the respective cylinder and subdivides the interior into an upper and a lower chamber; a cross-head element rigidly connecting the cylinders with one another for joint movement; workpiece engaging means on the support element and the cross-head element, respectively; and port means communicating with the upper and lower chambers for admitting fluid into and discharging it from the same, depending upon the direction in which the cylinders are to shift.

Due to the fact that the cylinders are rigidly connected for joint movement by means of the cross-head, the hydraulic control of their movements is very simple and requires only a servovalve. There is no necessity for providing complicated equipment to make the cylinders move in unison. Moreover, the cyliners are hydrostatically guided during their movement.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE is a somewhat diagrammatic vertical section illustrating a machine embodying the invention.

DESCRIPTION OF A PREFERRED EMBODIMENT

The machine shown in the FIGURE has a base or support 1 from which two uprights 2, 2' extend. The uprights 2, 2' are, in the illustrated embodiment, received in bores of the support 1 and are fixedly retained therein by means of clamping rings 11, 11' registered trademark of Ringfeder GmbH/Germany which are known per se and do not form a part of the invention.

At locations upwardly spaced from the support 1 the uprights are formed or otherwise provided with respective pistons 3, 3'. The upright 2 is surrounded by a cylinder 5 and the upright 2' is surrounded by a cylinder 5'. The pistons 3, 3' are located in the interiors of the respective cylinders 5, 5' and subdivide each interior into an upper chamber A and a lower chamber B. The cylinders thus in effect "float" with reference to the uprights 2, 2'. The latter are formed with internal passages (shown in broken lines); in each upright one of the passages communicates via a port 12 with the lower chamber B and the other passage communicates via a port 12' with the upper chamber A. The ports are connected via fluid lines (shown in broken lines) and a diagrammatically illustrated servovalve with a similarly diagrammatically illustrated source of pressure fluid and can be connected by the servovalve to a not-shown reservoir.

For rigidity the upper ends of the uprights 2, 2' are connected by a traverse member 4 which may, e.g., be plate-shaped.

The cylinders 5, 5' are rigidly connected with one another for joint movement by a cross-head 6.

A cylinder-and-piston unit 8 is mounted on the support 1 and carries a workpiece holder 9 (e.g., a chuck or the like); a similar workpiece holder 9' is carried by a cross-head 6.

In operation the cylinders 5, 5' are moved towards or away from the support 1 by a requisite distance which depends upon the length of a workpiece 10 that is to be tested. The workpiece is engaged by the holders 9, 9' and fine adjustments can be made by operating the hydraulic cylinder-and-piston unit 8. After the cylinders 5, 5' have reached the position required for a particular testing operation they are clamped in place so that they cannot move relative to the uprights 2, 2'. For this purpose the cylinders are each provided in this embodiment with two internal recesses through which the respective upright passes. Accommodated in each of these recesses is a hydraulically operable clamping sleeve 7, 7' registered trademark No. 897537 u. No. 897605 u. 05 - Germany Nr. 2031 425 which, when it has hydraulic pressure applied to it, clampingly engages the associated upright and prevents movement of the cylinder relative thereto. Once this clamping operation is in effect the adjustments can be carried out by operation of the cylinder-and-piston unit 8.

Because the hydrostatically guided cylinders 5, 5' are connected with one another by the cross-head 6, they move in unison without requiring complicated control mechanisms. Each of the cylinders 5, 5' of course operates as a double-acting cylinder, as will be readily understood from the drawing.

The cylinder-and-piston unit 8 could also be mounted on the cross-head 6, if desired, or two of these units could be provided one each on the support 1 and the cross-head 6, respectively. The presence of the single or dual units 8 makes it possible to obtain fine adjustment and to carry out testing in much smaller increments than would be otherwise feasible.

The machine according to the present invention is evidently simple in construction and can be readily manufactured in such a manner that a user can purchase it either supplied only with the uprights 2, 2' and with the cylinder-and-piston unit 8 (in which case the workpiece holder 9' would be mounted on the traverse member 4), or only with the cylinders 5, 5' and without the cylinder-and-piston unit 8 (in which case the workpiece holder 9 could be directly mounted on the support 1). Whenever desired, the missing features can then be added without requiring any reconstruction of the machine.

The machine according to the present invention will thus be seen to be ideally suited for such workpiece tests as the determination of tensile strength, workpiece behavior under compression, and analogous tests.

It will be understood that each of the elements described above, or two or more together, may also find a useful application in other types of applications differing from the types described above.

While the invention has been illustrated and described as embodied in a hydraulically operated workpiece testing machine, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A hydraulically operated workpiece testing machine, comprising a support element; at least two stationary uprights mounted on said support element and each provided with a piston; at least two floating cylinders, each shiftably surrounding one of said uprights so that the piston thereof is located in the interior of the respective cylinder and subdivides the interior into an upper and a lower chamber; a cross-head element rigidly connecting said cylinders with one another for joint movement; workpiece engaging means on said support element and said cross-head element, respectively; and port means communicating with said upper and lower chambers for admitting fluid into and discharging it from the same, depending upon the direction in which the cylinders are to shift.

2. A testing machine as defined in claim 1, wherein said uprights are each formed with fluid passages, and said port means comprises in each of said cylinders two ports which each communicate with one of said chambers and with said fluid passages.

3. A testing machine as defined in claim 1; and further comprising arresting means for arresting said cylinders in selectable positions relative to said uprights.

4. A testing machine as defined in claim 3, wherein said arresting means comprises hydraulically operated clamping sleeves.

5. A testing machine as defined in claim 1; and further comprising a vertically oriented cylinder-and-piston unit carried by one of said elements and in turn carrying said workpiece engaging means of said one element.

6. A testing machine as defined in claim 5, wherein said cylinder-and-piston unit is carried by said support element.

* * * * *